United States Patent
Hermanson

(10) Patent No.: US 6,783,356 B2
(45) Date of Patent: Aug. 31, 2004

(54) CANDLE STRUCTURE HAVING A DECORATIVE ANIMATED SCULPTURE

(75) Inventor: Terry Hermanson, New York, NY (US)

(73) Assignee: Mr. Christmas Incorporated, New York, NY (US)

( * ) Notice: Subject to any disclaimer, the term of this patent is extended or adjusted under 35 U.S.C. 154(b) by 0 days.

(21) Appl. No.: 10/287,621

(22) Filed: Nov. 5, 2002

(65) Prior Publication Data

US 2004/0086815 A1 May 6, 2004

(51) Int. Cl.⁷ .............................................. F21V 35/00
(52) U.S. Cl. .................... 431/126; 431/291; 362/35; 362/177; 362/806; 40/441; 446/210
(58) Field of Search ................................. 431/126, 289, 431/288, 291, 310; 362/35, 161, 177, 232, 806; 40/412, 422, 441; 446/210

(56) References Cited

U.S. PATENT DOCUMENTS

| | | | | | |
|---|---|---|---|---|---|
| 154,285 | A | * | 8/1874 | Schultze | 446/210 |
| 563,077 | A | * | 6/1896 | Senge | 446/210 |
| 589,173 | A | * | 8/1897 | Henke | 40/441 |
| 842,351 | A | * | 1/1907 | Stock | 446/210 |
| 939,705 | A | * | 11/1909 | Keller | 446/210 |
| 1,163,093 | A | * | 12/1915 | Krause | 446/210 |
| 1,521,448 | A | * | 12/1924 | Kragiel | 446/210 |
| 1,559,327 | A | * | 10/1925 | Kayashima et al. | 40/441 |
| 1,653,256 | A | * | 12/1927 | Davis | 362/415 |
| 2,840,689 | A | * | 6/1958 | Kazor | 362/35 |
| 3,711,698 | A |   | 1/1973 | Hess | 240/10.1 |
| 4,185,953 | A | * | 1/1980 | Schirneker | 431/291 |
| 5,032,360 | A |   | 7/1991 | Houston | 422/4 |
| 5,860,725 | A | * | 1/1999 | Zer et al. | 362/35 |
| 6,106,786 | A |   | 8/2000 | Akahoshi | 422/124 |
| 6,382,962 | B1 |  | 5/2002 | Papai | 431/291 |
| D462,132 | S |   | 8/2002 | Papai | D26/23 |
| D465,587 | S |   | 11/2002 | Papai | D26/23 |
| 6,629,836 | B2 |  | 10/2003 | Campbell | 431/33 |
| 2003/0129558 | A1 | | 7/2003 | Papai | 431/291 |

FOREIGN PATENT DOCUMENTS

| | | | | |
|---|---|---|---|---|
| DE | 3718369 A1 | * | 12/1988 | F21V/01/00 |
| EP | 1 030 113 |   | 8/2000 | F24C/7/00 |
| GB | 2170757 A | * | 8/1986 | A47G/23/00 |

* cited by examiner

Primary Examiner—Sara Clarke
(74) Attorney, Agent, or Firm—Fitzpatrick, Cella, Harper & Scinto

(57) ABSTRACT

A candle structure comprises a fan, wherein the heated air generated by a candle may propel the fan. The candle is housed in a container having a bottom wall and a side wall. The side wall is formed with vents located above the candle so that adequate air needed to permit the candle to combust can be drawn through the vent, thereby to enhance propulsion of the fan. The fan serves to impart a new functional and aesthetically pleasing characteristic to the basic candle structure by distributing the heat and the scent generated by the candle, while concurrently rotating decorative elements.

26 Claims, 2 Drawing Sheets

CANDLE STRUCTURE HAVING A DECORATIVE ANIMATED SCULPTURE

BACKGROUND OF THE INVENTION

1. Field of the Invention

The present invention relates to a candle structure, having a decorative animated sculpture, that is housed in a vented container that enhances the animated motion. More particularly the invention is directed to a candle housed in a vented container and a fan driven by rising heat from the burning candle.

2. Discussion of Related Art

The fundamental concepts and processes for making candles are well known. Candles typically have both utility and ornamental appeal. For example, the warm glow of a candle may provide light and heat. A scented candle may also provide a scent or an aroma and may mask odors, and a candle may generally serve as a decorative device. However, it is desirable to develop new ways of imparting novel, functional and aesthetically pleasing characteristics to the basic candle structure. U.S. patent application Publication No. 20020066687, for example, discloses a container with a lid comprising a decorative member which is a sports-related item, wherein the container may hold candles. U.S. Pat. No. 5,032,360 discloses an apparatus comprising a base with a candle mounted on it, and a container open at both ends located above the candle, wherein the container houses activated charcoal to filter odor-filled air.

The present invention further addresses the need to provide new functional and aesthetically pleasing characteristics to known candle structures.

SUMMARY OF THE INVENTION

The present invention provides for a candle structure having a decorative animated sculpture. The candle itself is housed in a vented container. At least one fan is mounted on the container above the candle, wherein heated air generated by and rising from the candle may continuously drive the fan. The fan may further serve to distribute the heat, and the scent or aroma generated by the candle. The fan may also serve to impart a new and aesthetically pleasing characteristic to the basic candle structure by carrying a decorative sculpture that rotates with it. The vents in the container permit air to readily reach the candle to aid in combustion of the candle fuel, and to enhance the flow of thus heated rising air to drive the fan.

In accordance with one aspect, the present invention is directed to a candle structure having a container comprising a hollow body with a bottom wall, with the hollow body defining an opening opposite the bottom wall, the container further comprising a cover or lid that can be removably mounted on the opening in the hollow body. The container further houses a candle, and is formed with at least one side vent or opening. The lid comprises at least one top vent or opening at a point where the lid is mounted on the opening in the hollow body. At least one fan is mounted on the lid on a bearing to permit it to be driven to rotate by rising heated air from the burning candle. The hollow body, lid and fan may further incorporate decorative elements. For example, a decorative sculpture may be mounted on the fan to be rotated with it. The candle may further comprise decorative elements, and/or a scent.

Thus, in accordance with this aspect, when the candle is lit, the surrounding air is heated, and the heated air rises and drives the fan. The air that aids combustion of the candle fuel can be readily replenished by unheated air drawn into the container through the vents in the hollow body, and vents in the lid, producing a "chimney-like" effect. In accordance with this aspect, the fan may further serve to distribute the scent and the heat from the candle.

In accordance with another aspect, the present invention is directed to a candle structure having a container comprising a hollow body with a bottom wall, with the hollow body defining an opening opposite the bottom wall. The container is provided a cover or lid that can be removably mounted on the opening in the hollow body. The container further houses a candle, and is formed with at least one side vent or opening within the hollow body. At least one fan can be mounted through a bearing on the lid. The hollow body, lid and fan may incorporate decorative elements. The candle may further have decorative elements, and/or a scent.

In accordance with this aspect, when the candle is lit, the surrounding air is heated, and the heated air rises and drives the fan. The air that aids combustion of the candle fuel is readily replenished by unheated air drawn into the container through the vents in the hollow body, again by a "chimney-like" effect. In accordance with this aspect, the fan may further serve to distribute the scent or heat from the candle. Movement of the fan may also move decorative elements.

In accordance with yet another aspect, the present invention is directed to a candle structure having a container comprising a hollow body with a bottom wall, with the hollow body defining an opening opposite the bottom wall. The container carries a lid that can be removably mounted on the opening in the hollow body. The hollow body is formed with at least one side vent or opening within the hollow body. The lid is formed to provide at least one top vent or opening at a point where the lid is mounted on the opening in the hollow body. At least one fan can be carried for rotation on a bearing mounted with the lid. The hollow body, lid and fan may also incorporate decorative elements.

In accordance with this aspect, when a candle is mounted in the vented container and lit, the surrounding air is heated, and the heated air rises and drives the fan to rotate. The air within the container is replenished by unheated air drawn into the container through the vents in the hollow body, and vents in the lid. In accordance with this aspect, the fan may also distribute scent and heat from the candle, and the fan can drive decorative elements carried on it.

An advantage of the present invention is that the vents allow for continuous replenishment of the air within the container, thereby providing a continuous source of heated air to drive the fan and any decorative elements attached thereto. Another advantage of the present invention is that the rotating fan may distribute heat and scent generated by the burning candle.

BRIEF DESCRIPTION OF THE DRAWINGS

The foregoing and other aspects of the present invention will best be appreciated with reference to the detailed description of the invention taken in conjunction with the accompanying drawings, wherein.

DETAILED DESCRIPTION OF PREFERRED EMBODIMENTS

The present invention is directed to a candle structure having an advantageously vented container and comprising at least one fan, wherein the heated air generated by a burning candle in the container may continuously drive the fan to rotate. The vents serve to continuously replenish the air in the container to aid combustion of the candle fuel. The fan may further serve to distribute the heat and the aroma generated by the candle. The fan may also serve to impart a new and aesthetically pleasing characteristic to the basic candle structure by concurrently rotating decorative elements mounted on it.

While the present invention may take the form of a number of exemplary embodiments, for ease of explanation, one such embodiment will be described in detail.

Figure 1:
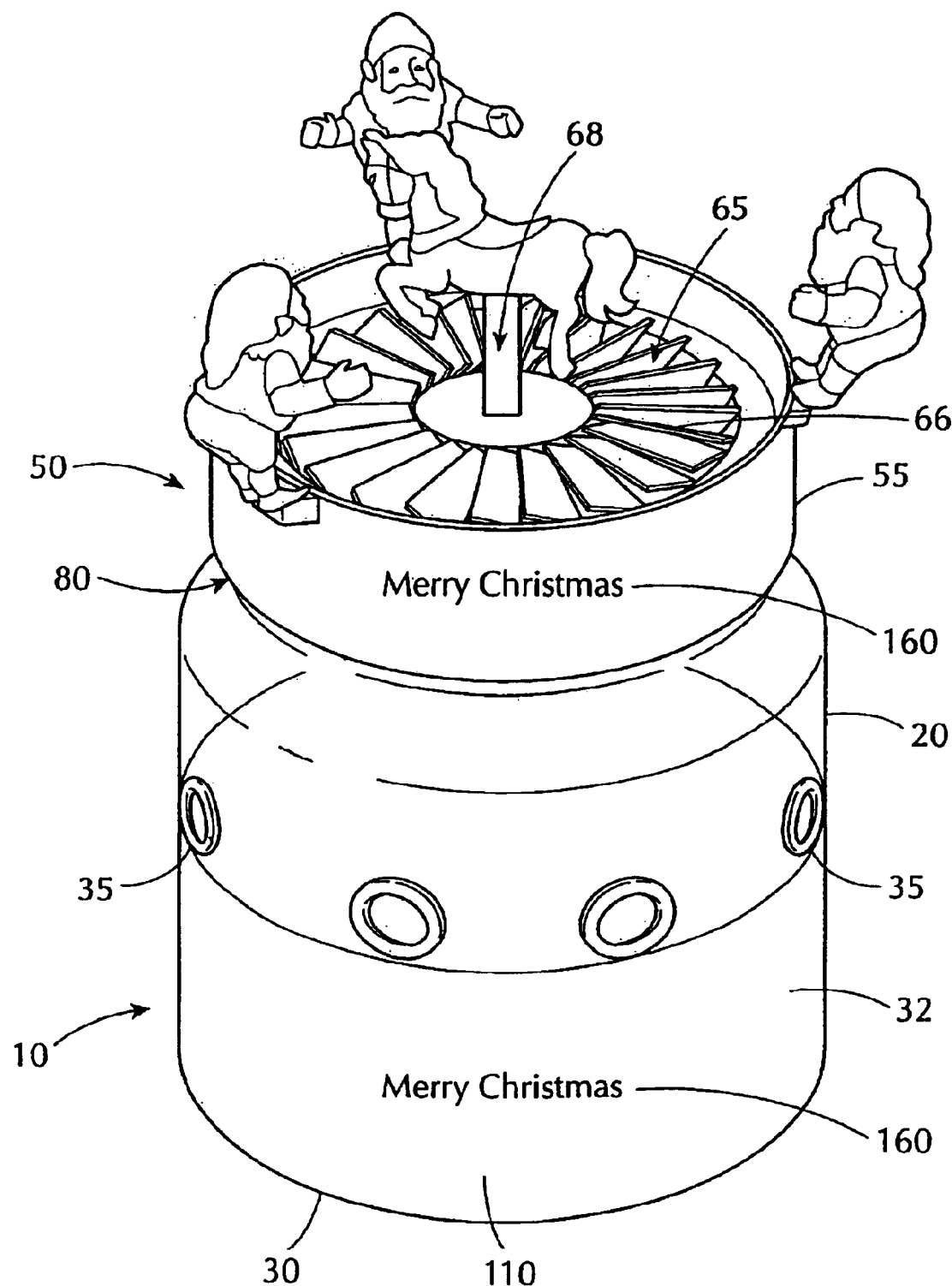
FIG. 1 is a perspective view of an exemplary embodiment of the candle structure having a container carrying at least one fan, in accordance with the present invention. Both the hollow body and the lid are formed with at least one vent, and decorative elements have been added to both the fan and the lid.

Referring to the figures, wherein like numerals indicate the same element throughout the views, there is shown in FIG. 1 a candle structure including a vented container 10, comprising a hollow body 20 with a bottom wall 30 and a side wall 32. As shown, the body is generally cylindrical, but, of course, may take other shapes. At least one and preferably a large number, such as eight, side vents 35 are formed in the side wall 32 of the hollow body 20.

Figure 2:
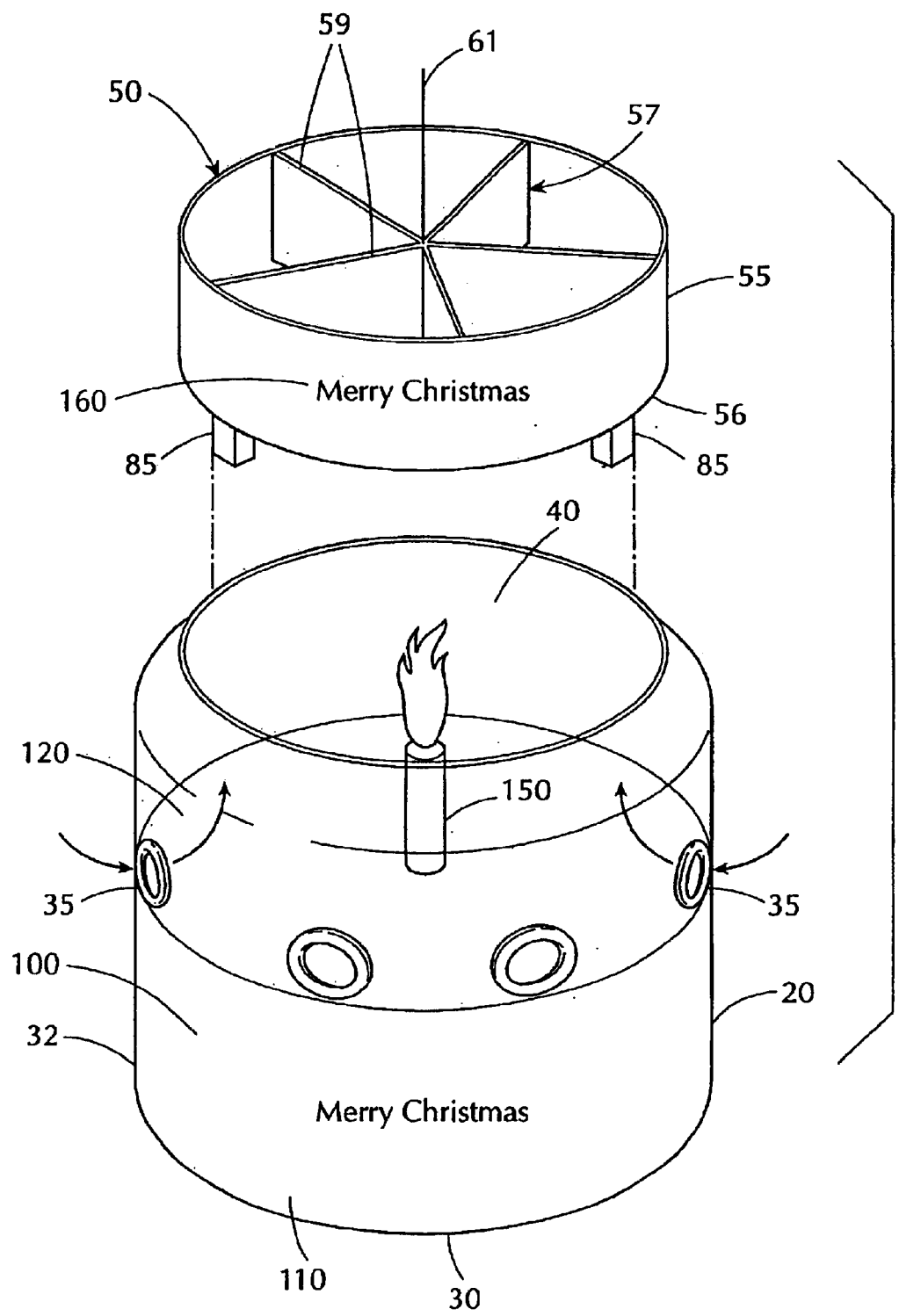
FIG. 2 is an exploded perspective view of an exemplary embodiment of the candle structure, in accordance with the present invention, wherein the lid has been removed.

As illustrated in FIG. 2, the hollow body 20 also defines a top opening 40 opposite the bottom wall 30.

The candle structure including a vented container 10 further comprises a cover or lid 50 that can be removably mounted in the opening 40. The lid 50 includes a side wall 55 that also is generally cylindrical. However, the side wall 55 of the lid may take other shapes, such as one which matches that of the hollow body. The lid side wall 55 supports a frame 57 that includes a number of radially extending legs 59 that are joined at the central vertical axis of the lid. A needle 61, which is one component of a needle bearing, is mounted on the junction of the legs 59 of the frame 57 to project upwardly substantially along the axis of the lid, and thus the hollow body 20, when the lid 50 is mounted on it.

As shown in FIG. 1, the lid 50 also includes a lightweight fan 65 having a number of blades 66 and a needle bearing socket 68 at its center that receives the needle 61 mounted on the legs 59, as illustrated in FIG. 2.

As illustrated in FIG. 1, the candle structure including a vented container 10 further comprises at least one top vent 80 at the location where the lid 50 is mounted in the opening 40. As illustrated in FIG. 2, in this exemplary embodiment, the top vents 80 are formed by at least three feet 85 attached to the bottom 56 of the side wall 55 of the lid 50. When the lid 50 is placed in the opening 40 of the hollow body 20, the feet 85 elevate the lid 50 above the hollow body 20, thereby creating the top vents 80.

As illustrated in FIG. 2, the candle structure 10 further comprises a candle 100 with a bottom portion 110 and a top portion 120, wherein the bottom portion 110 of the candle 100 is substantially in contact with the bottom wall 30 of the hollow body 20. The top portion 120 of the candle 100 comprises at least one wick 150. The candle may further comprise an aroma or a scent. The candle structure 10 may further comprise a written message 160 on the outer surface of the candle 100, the hollow body 20, and/or the lid 50.

As illustrated in FIG. 2, when the wick 150 in the top portion 120 of the candle 100 in the candle structure 10 is lit, the heated air generated around the flame rises, and is constantly replenished by ambient air drawn into the candle structure 10, through the side vents 35, and the top vents 80. The rising hot air propels the fan 65, on the lid 50, as illustrated in FIG. 1. The fan 65 may then distribute the heat, and the scent or aroma generated by the candle, thereby generating a functional and aesthetically pleasing result.

The hollow body 20 and the bottom wall 30 may be made in any suitable shape and/or configuration, and may be made from any suitable material, such as non-flammable plastic or glass. The hollow body 20 may be made in any suitable color or transparency, and is preferably clear. The hollow body 20 may comprise suitable decorative elements. The side vent 35 may be made in any suitable shape or configuration and is preferably round or oval. The side vent 35 may be of any suitable size, and is preferably of sufficient size to allow adequate replenishment of combustion air to the container. The opening 40 opposite the bottom wall 30 of the hollow body 20 may be of any suitable size, shape or configuration, and does not need to conform to the size, shape or configuration of the bottom wall 30.

The lid 50 may be of any suitable size, shape, configuration, color or transparency, and may comprise suitable decorative elements. The lid 50 may be made of any suitable material, and is preferably made of a non-flammable material. The fan 65 may be of any suitable configuration, and may comprise a number of different decorative elements. The top vent 80 is of any suitable shape or configuration, and is preferably also of sufficient size to allow adequate replenishment of the combustion air in the container. The top vents 80 may be created in any suitable manner, and may preferably be created by attaching feet 85 to the bottom 56 of the side wall 55 of the lid 50.

The candle 100 also can be made in any suitable configuration, including cylindrical, circular, quadrilateral and polygonal, and in any variation thereof, and is preferably cylindrical, which configuration is also known as a pillar candle or column candle. The candle 100 can be made from known materials, and is preferably made from wax or paraffin. The candle may comprise means for evenly or selectively melting the candle, such as the positioning of the one or more wicks 150 within the candle 100, or this may be achieved by the composition of the candle 100 itself.

Although shown and described are what are believed to be the preferred embodiments of the candle in accordance with the invention, it is apparent that departures from specific designs and methods described and shown will suggest themselves to those skilled in the art and may be used without departing from the spirit and scope of the invention. The present invention is not restricted to the particular constructions described and illustrated, but should be construed to encompass all modifications that may fall within the scope of the following claims.

That which is claimed is:

1. A candle structure comprising:

a candle having a top portion and a bottom portion;

a hollow body having a bottom wall, and a side wall, said bottom portion of said candle being substantially in contact with said bottom wall, said hollow body defining an opening opposite said bottom wall, said hollow body being formed with at least one side vent in said side wall;

a lid structure configured to be removably mounted in said opening in said hollow body, said lid structure comprising a side wall, and at least one fan; and bearing means for mounting said fan for rotation with said lid structure, wherein heat generated by said candle when combusting rises to propel said fan to rotate, and wherein air permitting combustion of said candle can enter said hollow body through said side vent.

2. The candle structure of claim 1, further comprising at least one top vent at a location where said lid is removably mounted in said opening in said hollow body.

3. The candle structure of claim 1, wherein said candle further comprises a scent.

4. The candle structure of claim 1, wherein said candle further comprises decorative elements.

5. The candle structure of claim 1, wherein said hollow body further, comprises decorative elements.

6. The candle structure of claim 1, wherein said lid structure further comprises decorative elements.

7. The candle structure of claim 1, wherein said fan further comprises decorative elements.

8. The candle structure of claim 1, further comprising a written message on the exterior of said candle, said hollow body or said lid.

9. The candle structure of claim 1, wherein said bearing means comprises a needle mounted on one of said lid structure and said fan and a needle socket mounted on the other of said lid structure and said fan to receive said needle.

10. A candle structure comprising:
   a hollow body having a bottom wall, and a sidewall, said hollow body defining an opening opposite said bottom wall, said hollow body being formed with at least one side vent in said side wall;
   a lid structure configured to be removably mounted in said opening in said hollow body, said lid structure comprising a side wall and at least one fan; and
   bearing means for mounting said fan for radiation with said lid structure, wherein heat generated by a candle, held in said hollow body, when combusting can rise to propel said fan to rotate, and wherein air permitting combustion of said candle can enter said hollow body through said side vent.

11. The candle structure of claim 10, further comprising at least one top vent located where said lid is removably mounted in said opening in said hollow body.

12. The candle structure of claim 10, wherein said hollow body further comprises decorative elements.

13. The candle structure of claim 10, wherein said lid structure further comprises decorative elements.

14. The candle structure of claim 10, wherein said fan further comprises decorative elements.

15. The candle structure of claim 10, further comprising a written message on the exterior of said hollow body or said lid.

16. The candle structure of claim 10, wherein said bearing means comprises a needle mounted on one of said lid structure and said fan, and a needle socket mounted on the other of said lid structure and said fan to receive said needle.

17. For use with a candle, the improvement comprising:
   a hollow body having a bottom wall, and a side wall, a bottom portion of a candle being substantially in contact with said bottom wall, said hollow body defining an opening opposite said bottom wall, said hollow body being formed with at least one side vent in said side wall;
   a lid structure configured to be removably mounted in said opening in said hollow body, said lid structure comprising a side wall and at least one fan; and
   bearing means for mounting said fan for rotation with said lid structure, wherein heat generated by said candle when combusting rises to propel said fan to rotate, and wherein air permitting combustion of said candle can enter said hollow body through said side vent and said top vent.

18. For use with a candle, the improvement comprising:
   a hollow body having a bottom wall, and a side wall, a bottom portion of a candle being substantially in contact with said bottom wall, said hollow body defining an opening opposite said bottom wall, said hollow body being formed with at least one side vent in said side wall;
   a lid structure configured to be removably mounted in said opening in said hollow body, said lid structure comprising a side wall and at least one fan;
   at least one top vent located where said lid is removably mounted in said opening in said hollow body; and
   bearing means for mounting said fan for rotation with said lid structure, wherein heat generated by said candle when combusting rises to propel said fan to rotate, and wherein air permitting combustion of said candle can enter said hollow body through said side vent and said top vent.

19. A decorative container for a candle comprising:
   a hollow body for holding the candle, said hollow body having a bottom wall and a side wall defining an opening generally opposed to said bottom wall, said side wall being formed with at least one vent;
   a lid structure configured to be removably mounted on said side wall of said hollow body in said opening, said lid structure comprising a side wall and a first bearing member mounted with said side wall; and
   a fan configured to be mounted with said side wall of said lid structure and having a second bearing member adapted to engage said first bearing member thereby to mount said fan for rotation relative to said lid structure,
   wherein heat generated by a candle held in said hollow body when combusting rises to propel said fan to rotate, and wherein air permitting combustion of the candle can enter said hollow body through said vent.

20. The decorative container for a candle according to claim 19, further comprising means for removably mounting said side wall of said lid structure in the opening defined by said side wall of said hollow body to space said side wall of said lid structure from said side wall of said hollow body thereby to define a second vent for admitting air to said container.

21. The decorative container for a candle according to claim 20, wherein said mounting means comprises a plurality of feet formed on one of said lid structure and said hollow body, thereby to space said side wall of said hollow body from said side wall of said lid structure.

22. The decorative container for a candle according to claim 19, wherein one of said first bearing member and said second bearing member comprises a needle and the other of said first bearing member and said second bearing member comprises a needle socket for receiving said needle.

23. The decorative container for a candle according to claim 22, wherein said needle is mounted with said side wall of said lid structure to project upwardly, and said needle socket is mounted with said fan to project upwardly but open downwardly, whereby bearing engagement between said needle and said needle socket is above said fan.

24. A lid assembly adapted for use with a decorative container for a candle, the container having a hollow body for holding the candle, the hollow body including a bottom wall and a side wall defining an opening generally opposed to said bottom wall; said lid assembly comprising:
   a lid structure having a side wall, and a first bearing member mounted with said side wall;

a fan configured to be mounted with said side wall of said lid structure and having a second bearing member adapted to engage said first bearing member thereby to mount said fan for rotation relative to said lid structure; and means for mounting said side wall of said lid structure with the side wall of the hollow body thereby to space the two apart and define a vent therebetween.

25. The lid assembly according to claim 24, wherein said mounting means comprises a plurality of feet associated with said lid structure, thereby to space said side wall of said hollow body from said side wall of said lid structure.

26. The lid assembly according to claim 24, wherein said needle is mounted with said side wall of said lid structure to project upwardly and said needle socket is mounted with said fan to project upwardly but open downwardly, whereby bearing engagement between said needle and said needle socket is above said fan.

* * * * *

UNITED STATES PATENT AND TRADEMARK OFFICE
CERTIFICATE OF CORRECTION

PATENT NO. : 6,783,356 B2
DATED : August 31, 2004
INVENTOR(S) : Terry Hermanson

It is certified that error appears in the above-identified patent and that said Letters Patent is hereby corrected as shown below:

<u>Column 5,</u>
Line 10, "further," should read -- further --; and
Line 30, "radiation" should read -- rotation --.

Signed and Sealed this

Twenty-second Day of March, 2005

JON W. DUDAS
*Director of the United States Patent and Trademark Office*